United States Patent [19]

Okamura et al.

[11] Patent Number: 4,511,644

[45] Date of Patent: Apr. 16, 1985

[54] PHOTOGRAPHIC ELEMENTS WITH DEVELOPMENT INHIBITOR PRECURSOR

[75] Inventors: Hisashi Okamura; Shinji Sakaguchi; Osamu Takahashi; Ashita Murai, all of Kanagawa, Japan

[73] Assignee: Fuji Photo Film Co., Ltd., Kanagawa, Japan

[21] Appl. No.: 560,054

[22] Filed: Dec. 9, 1983

[30] Foreign Application Priority Data

Dec. 10, 1982 [JP] Japan ................. 57-216690

[51] Int. Cl.$^3$ .................. G03C 5/54; G03C 1/40; G03C 1/34
[52] U.S. Cl. ..................... 430/219; 430/445; 430/544; 430/559; 430/611; 430/957; 430/960
[58] Field of Search ............ 430/219, 382, 445, 544, 430/611, 957, 960, 559

[56] References Cited

U.S. PATENT DOCUMENTS

| | | | |
|---|---|---|---|
| 3,084,044 | 4/1963 | Dersch et al. | 430/487 |
| 3,260,597 | 7/1966 | Weyerts et al. | 430/219 |
| 4,246,333 | 1/1981 | Fuseya et al. | 430/219 |
| 4,355,101 | 10/1982 | Mehta et al. | 430/219 |
| 4,390,613 | 6/1983 | Mehta et al. | 430/219 |

FOREIGN PATENT DOCUMENTS 2427183 12/1974 Fed. Rep. of Germany ...... 430/219

*Primary Examiner*—Richard L. Schilling
*Attorney, Agent, or Firm*—Sughrue, Mion, Zinn Macpeak & Seas

[57] ABSTRACT

A photographic element comprised of a support having provided thereon at least one silver halide emulsion layer, the element containing a development inhibitor precursor. The development inhibitor precursor is represented by the following general formula (I):

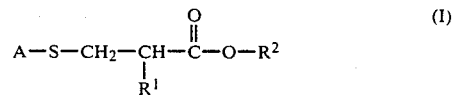

wherein A represents an unsubstituted or substituted phenyl group or a 5-membered or 6-membered nitrogen-containing heterocyclic ring; $R^1$ represents a hydrogen atom or a monovalent substituent; and $R^2$ represents an organic ballasting group. The element is capable of providing color images having improved image quality particularly with respect to having a low density in the Dmin areas. The photographic element can be processed over a wide range of processing temperatures. Further, the element can be preserved for long periods of time without having a reduction in the density in the Dmax areas.

15 Claims, No Drawings

PHOTOGRAPHIC ELEMENTS WITH DEVELOPMENT INHIBITOR PRECURSOR

FIELD OF THE INVENTION

This invention relates to a photographic element and particularly, to a photographic element using a development inhibitor precursor. More particularly, the invention relates to a color diffusion transfer photographic element using a development inhibitor precursor.

BACKGROUND OF THE INVENTION

U.S. Pat. Nos. 3,260,597 and 3,265,498 disclose controlling the density of a Dmin range referred to as "fog" by using a development inhibitor or a development inhibitor precursor in a color diffusion transfer photographic element.

In these patents, the density of the Dmin region which is effected by the acting time is controlled by using a development inhibitor for an image-receiving layer or the acting time of a development inhibitor is controlled by using a precursor capable of releasing a development inhibitor in a hydrolysis reaction. However, the compounds illustrated in these patents inhibit not only the unnecessary development but also the necessary development, whereby the image quality is greatly reduced.

Furthermore, the photographic development reaction is greatly influenced by temperature, i.e., development proceeds slowly at low temperature but proceeds quickly at high temperature. In particular, excessive development is liable to occur at high temperature, whereby the density in a Dmin region increases which results in greatly reducing image quality. Accordingly, it has been desired to find a development inhibitor precursor which can enlarge the allowable processing temperature region by inhibiting the occurrence of unnecessary development at about room temperature, controlling the necessary development so that the development is not inhibited, and inhibiting the occurrence of excessive development at high temperature.

Japanese Patent Publication No. 17369/80 and Japanese Patent Publication (Unexamined) No. 77842/81 disclose development inhibitor precursors for controlling the acting time of development inhibitors by controlling the reaction rate of hydrolysis.

Furthermore, Japanese Patent Publication (Unexamined) No. 130929/79 discloses a development inhibitor precursor which suppresses the occurrence of unnecessary development only by controlling the reaction rate of hydrolysis by temperature, that is, by restraining the increase of the reaction rate of hydrolysis below about room temperature beyond what is necessary and also enlarge the allowable region of processing temperature by sufficiently increasing the reaction rate of hydrolysis at high temperature to control the occurrence of excessive development.

However, the compounds illustrated in the foregoing Japanese Patent Publication No. 17369/80 and Japanese Patent Publication (Unexamined) Nos. 77842/81 and 130929/79 cause a reduction in density in the maximum color density (Dmax) region of an image when these compounds are incorporated in photographic elements and preserved in such a state, which results in greatly reducing image quality. Also, when the photographic elements using these development inhibitor precursors are preserved for a long period of time or are preserved at a high temperature and/or a high humidity, the reduction in image quality becomes greater to the extent that it substantially reduces the commercial value of the photographic elements.

Considering the molecular weights of the compounds illustrated in the foregoing patent publications, it is considered to be reasonable that these compounds unavoidably diffuse in the photographic elements and they diffuse more and more when the photographic elements are preserved for a long period of time although the details have not yet been clarified.

On the other hand, in Japanese Patent Publication No. 34927/80 and Japanese Patent Publication (Unexamined) No. 138745/80, there are illustrated organic ballasting group-containing development inhibitor precursors which become substantially nondiffusible in photographic elements.

However, when a photographic element containing such a development inhibitor precursor having an organic ballasting group as illustrated in the foregoing patent publications is preserved for a long period of time, the density at the Dmax areas is also reduced, which results in greatly reducing image quality. The reason is believed to be that since these compounds are substantially nondiffusible, the releasing rate of development inhibitors by hydrolysis is undesirable.

SUMMARY OF THE INVENTION

A primary object of this invention is to provide a development inhibitor precursor-containing color diffusion transfer photographic element giving color images having improved image quality (in particular, color images having a low density at the Dmin areas).

Another object of this invention is to provide a development inhibitor precursor-containing color diffusion transfer photographic element having a wide allowable range of processing temperature.

Still another object of this invention is to provide a development inhibitor precursor-containing color diffusion transfer photographic element which can be preserved for a long period of time without being accompanied by reduction in density at the Dmax areas.

As the result of various investigations, the inventors have discovered that the above-described objects of this invention can be attained by using a novel development inhibitor precursor shown by following general formula (I):

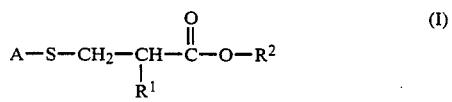

wherein A represents an unsubstituted or substituted phenyl group or a 5-membered or 6-membered nitrogen-containing heterocyclic ring; $R^1$ represents a hydrogen atom or a monovalent substituent; and $R^2$ represents an organic ballasting group.

That is, according to this invention, there is provided a photographic element comprising a support having provided thereon at least one photosensitive silver halide emulsion layer, the photographic element containing the development inhibitor precursor shown by foregoing general formula (I).

DESCRIPTION OF THE PREFERRED EMBODIMENT

In general formula (I), A represents an unsubstituted or substituted phenyl group or a 5-membered or 6-membered nitrogen-containing heterocyclic ring.

Examples of the substituent for the substituted phenyl group shown by A are an alkyl group (preferably, an alkyl group having 1 to 4 carbon atoms, e.g., a methyl group, an ethyl group, etc.), an alkoxy group (preferably, an alkoxy group having 1 to 4 carbon atoms, e.g., a methoxy group, an ethoxy group, etc.), a nitro group, a halogen atom (e.g., a chlorine atom, etc.), an alkoxycarbonyl group (in which the alkyl moiety thereof preferably has 1 to 4 carbon atoms, e.g., a methoxycarbonyl group, an ethoxycarbonyl group, etc.), an unsubstituted or substituted carbamoyl group (in which the substituent thereof is preferably an alkyl group having 1 to 4 carbon atoms, a phenyl group, etc.), and an unsubstituted or substituted sulfamoyl group (in which the substituent thereof is preferably an alkyl group having 1 to 4 carbon atoms, a phenyl group, etc.).

The nitrogen-containing heterocyclic ring shown by A may be fused with a benzene ring, etc., or may be substituted by an ordinary substituent (e.g., a phenyl group, etc.). Examples of the nitrogen-containing heterocyclic ring are tetrazole rings such as a tetrazole ring, a phenyltetrazole ring, etc.; triazole rings such as a benzotriazole ring, a 1,2,4-triazole ring, etc.; diazole rings such as a benzimidazole ring, an imidazole ring, etc.; pyrimidine rings such as a pyrimidine ring, etc.; and monoazole rings such as a benzothiazole ring, a benzoxazole ring, etc. Preferred are nitrogen-containing heterocyclic rings having at least two different atoms, such as tetrazole rings, benzotriazole rings, and benzothiazole rings, with the tetrazole rings, especially a phenyltetrazole ring, being particularly preferred.

In a preferred embodiment of this invention, the photographic element of this invention is a color diffusion transfer photographic element having at least one photosensitive silver halide emulsion layer having a dye image-forming compound associated therewith, a support for supporting the silver halide emulsion layer and an image-receiving layer, which photographic element contains a development inhibitor precursor, the development inhibitor precursor being the compound shown by foregoing general formula (I).

In another preferred embodiment of this invention, the photographic element containing the development inhibitor precursor shown by general formula (I) is a color diffusion transfer photographic element comprising a support, a photosensitive element having at least one silver halide emulsion layer and a dye image-forming compound associated therewith, and an image-receiving element fixing a diffusible dye formed from the dye image-forming compound to form an image; and further comprising other hydrophilic colloid layers, if desired, an alkaline processing composition capable of developing the exposed photosensitive element, and a neutralizing means for neutralizing the alkaline processing composition, if desired.

In still another preferred embodiment of this invention, the photographic element of this invention containing the development inhibitor precursor shown by general formula (I) is a color diffusion transfer photographic element including a photosensitive sheet comprising a transparent support having provided thereon an image-receiving element for fixing a diffusible dye to form an image, a white reflecting layer, a light-shielding layer, and a photosensitive element containing at least one silver halide emulsion layer having a dye image-forming compound associated therewith; an alkaline processing composition capable of developing the exposed photosensitive element; and a cover sheet comprising another support having provided thereon a neutralizing means for neutralizing the alkaline processing composition.

The compounds of general formula (I) will now be explained in more detail.

Preferred 5-membered or 6-membered nitrogen-containing heterocyclic ring shown by A in general formula (I) is a compound represented by general formula (II):

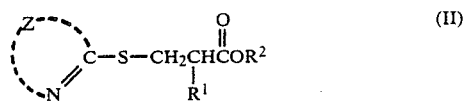

wherein Z represents a non-metallic atomic group necessary for completing a 5- or 6-membered heterocyclic ring.

The heterocyclic ring may be substituted, and examples of the substituent are an alkyl group such as a methyl group; an aryl group such as a phenyl group; and an aralkyl group such as a benzyl group. Also, each of these alkyl group, aryl group, and aralkyl group may be further substituted with ordinary substituents which do not disturb the action as a development inhibitor.

$R^1$ in general formula (II) represents a hydrogen atom or a monovalent substituent. Examples of the monovalent substituent are a halogen atom (e.g., a fluorine atom, a chlorine atom, a bromine atom, etc.), a carbamoyl group, a sulfamoyl group, a carboxy group, an unsubstituted or substituted alkyl group which may be straight or branched chain (preferably, an alkyl group having 1 to 30 carbon atoms), an unsubstituted or substituted aryl group (e.g., a phenyl group, a naphthyl group, etc.), and an unsubstituted or substituted aralkyl group (e.g., a benzyl group, a phenethyl group, etc.).

In foregoing $R^1$ examples of the substituents for the alkyl group, aryl group, and aralkyl group are an alkoxy group (preferably, an alkoxy group having 1 to 8 carbon atoms, e.g., a methoxy group, an ethoxy group, etc.), a hydroxy group, a carboxy group, a carbamoyl group, a sulfamoyl group, and a halogen atom (e.g., a chlorine atom, a fluorine atom, etc.).

As the heterocyclic ring formed by Z in general formula (II), there are the nitrogen-containing heterocyclic rings illustrated as the examples of A in general formula (I).

The organic ballasting group shown by $R^2$ may be a substituent capable of rendering the compound substantially non-diffusible in the layer constituting the photographic element. The substituent is not restricted provided it can render the compound non-diffusible. An ordinary ballasting group includes an alkyl group, an aryl group, an aralkyl group, etc. A useful ballasting group usually has at least 8 carbon atoms and examples of such ballasting group include an unsubstituted or substituted alkyl group having 8 to 32 carbon atoms, an unsubstituted or substituted aryl group, and an unsubstituted or substituted aralkyl group.

Any substituents can be employed as the substituents for the foregoing alkyl group, aryl group, and aralkyl group if the compound having such $R^2$ is non-diffusible and specific examples of these substituents are those illustrated in regard to $R^1$.

The useful development inhibitor precursor used in this invention usually splits in an alkali solution to release a development inhibitor capable of diffusing in the alkali solution.

Typical examples of the useful development inhibitor precursor used in this invention are as follows:

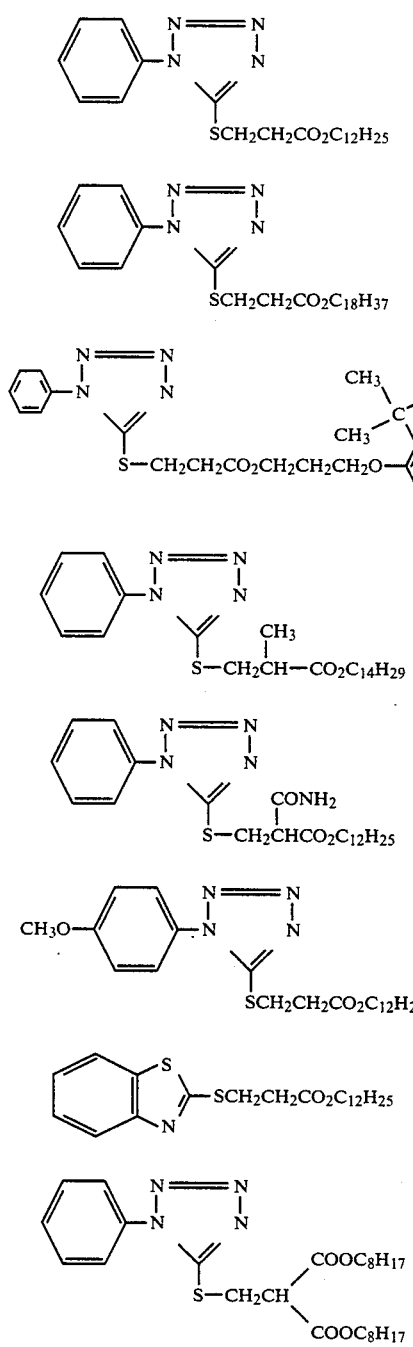

Of these compounds, Compounds 1, 2, 3, and 5 are preferred.

These compounds as illustrated above can be generally prepared by adding a mercaptan shown by following general formula (IV) to unsaturated esters shown by general formula (III):

wherein $R^1$, $R^2$, and A have the same meaning as in general formula (I).

Practical examples for producing these compounds are illustrated below.

Synthesis of Compound 1

In a 300 ml three-necked flask equipped with a stirrer and a Dimroth condenser were placed 6.95 g of 1-phenyl-5-mercaptotetrazole, 7.21 g of dodecyl acrylate, 3.2 g of sodium acetate, and 50 ml of acetic acid, and the mixture was stirred for 15 hours while heating at 60° to 70° C. After adding 200 ml of ethyl acetate to the reaction mixture, the mixture was poured into a 500 ml separatory funnel. After washing twice with 200 ml of water, the mixture was further washed with a saturated aqueous solution of sodium hydrogencarbonate until the generation of carbon dioxide gas stopped.

To the ethyl acetate solution thus obtained was added magnesium sulfate, and after allowing the mixture to dry overnight, the mixture was concentrated under reduced pressure. The resulting mixture was subjected to column chromatography with silica gel (developing solvent: hexane/ethyl acetate=8/1) to separate a desired product. The solvent was distilled off under reduced pressure to obtain Compound 1 which was a colorless, transparent, and viscous liquid. The yield was 10.3 g, which was 82% of the theoretical value. The structure of the product was confirmed by the NMR spectra, IR spectra, and MS spectra.

Synthesis of Compound 2

After performing the same reaction procedure as in the case of producing Compound 1 in acetic acid, 100 ml of methanol was added to the reaction mixture, followed by ice-cooling, whereby crystals were deposited. The crystals were collected, air-dried, and recrystallized from methanol to obtain Compound 2. The yield was 12.0 g, which was 78% of the theoretical value. The melting point was 45° to 46° C. The structure was confirmed by the NMR spectra, IR spectra, and MS spectra.

Other development inhibitor precursors used in this invention could be prepared by similar methods to the above-described methods.

In a preferred embodiment of this invention, the photosensitive element is comprised of a support having provided thereon at least one layer containing a silver halide emulsion and has the development inhibitor precursor shown by foregoing general formula (I) so that the precursor can effectively act.

In a very preferred embodiment of this invention, the photographic element of this invention includes:

(1) a photosensitive layer containing at least one silver halide emulsion layer having a dye image-forming compound associated therewith, (2) an image-receiving layer, (3) a means for releasing an alkaline processing composition containing a silver halide developing agent, (4) a neutralizing means including a neutralizing layer having, if desired, a neutralization timing layer associated therewith, and (5) the development inhibitor precursor shown by foregoing general formula (I) added so that the precursor effectively acts on the development of the foregoing silver halide emulsion layer.

If the development inhibitor precursor shown by foregoing formula (I) is associated so that the precursor effectively acts on the development of the silver halide emulsion, the precursor may be incorporated in any layer or layers but is preferably incorporated in a photosensitive layer such as a layer containing a silver halide emulsion, a layer containing a dye image-forming compound, and other auxialiary layers; an image-receiving layer or an auxialiary layer such as a white reflecting layer; or a neutralizing means such as a neutralizing layer or a neutralization timing layer. It is particularly preferred that the development inhibitor precursor be incorporated in a neutralizing layer or a neutralization timing layer.

The amount of the foregoing development inhibitor precursor added in a diffusion transfer photographic process depends upon the amount of developer, development conditions, the formulation of the silver halide emulsion layer, etc. and cannot be unequivocally defined. But it is usually at least $10^{-5}$ mol, preferably $10^{-4}$ to $10^{-1}$ mol, per mol of silver in the silver halide emulsion layer or layers.

The development inhibitor precursor may be incorporated in a desired layer by a technically applicable effective method. In a preferred embodiment, the development inhibitor precursor can be added to a coating composition of a desired layer as a solution in an organic solvent such as acetone, etc., or may be dissolved in a high boiling solvent such as a water-insoluble coupler solvent, and then added to a coating composition as an emulsified dispersion of the solution in a carrier medium. Typical examples of the useful coupler solvent are proper polar solvents such as liquid dye stabilizers as described in the article entitled "Improved Photographic Dye Image Stabilizer-Solvent" in Product Licensing Index, Vol. 83, March, 1971, tri-o-cresyl phosphate, di-n-butyl phthalate, diethyllaurylamide, 2,4-diarylphenyls, etc.

In another preferred embodiment, the development inhibitor precursor is directly dissolved in a coating composition using an organic solvent for a neutralizing layer, a neutralization timing layer, etc. when coating the coating composition.

Various addition methods for the development inhibitor precursor were described above but other methods may also be employed without being restricted to the foregoing methods.

When the photographic element of this invention is applied to a color diffusion transfer photographic process, the photographic element may have a constitution of a peel-apart type film unit; an integrated type film unit as disclosed in Japanese Patent Publication Nos. 16356/71 and 33697/73, Japanese Patent Publication (Unexamined) No. 13040/75, and British Pat. No. 1,330,524; and a peeling-unnecessary type film unit as disclosed in Japanese Patent Publication (Unexamined) No. 119345/82.

With all these types of film units, it is desirable to increase the allowable range of a processing temperature to use a polymer layer protected by a neutralization timing layer.

As the neutralizing timing layer, ordinary known timing layers can be used.

Useful materials for such a timing layer include a polymer having a low alkali permeability, such as polyvinyl alcohol, cellulose acetate, partially hydrolyzed polyvinyl acetate, etc.; a polymer prepared by copolymerizing a small amount of a hydrophilic comonomer such as an acrylic acid monomer; a polymer having a lactone ring; and the like.

Particularly useful materials for the timing layer are the cellulose acetates as disclosed in Japanese Patent Publication (Unexamined) Nos. 136328/79 and 130926/79, U.S. Pat. Nos. 4,009,030 and 4,029,849, etc.; the polymers prepared by copolymerizing a small amount of a hydrophilic comonomer such as acrylic acid, etc. as disclosed in Japanese Patent Publication (Unexamined) Nos. 145217/77, 72622/78, 78130/79, 138433/79, 138432/79 and 128335/79, U.S. Pat. Nos. 4,061,496, etc.; and the polymers having a lactone ring as disclosed in Japanese Patent Publication (Unexamined) No. 54341/80 and Research Disclosure, No. 18, 452 (1979).

Other materials used for the timing layer in this invention are also disclosed in U.S. Pat. Nos. 3,455,686, 4,009,030, 3,785,815 and 4,123,275, Japanese Patent Publication (Unexamined) Nos. 92022/73, 64435/74, 22935/74, 77333/76, 2431/77 and 88330/77, Japanese Patent Publication Nos. 15756/69, 12676/71 and 41214/73, West German Offenlegungschrift Nos. 1,622,936 and 2,162,277, and Research Disclosure, 15,162, No. 151 (1976).

A development inhibitor can be released from the development inhibitor precursor of this invention by contacting the precursor with an alkaline medium, but splitting of the development inhibitor precursor can be achieved or accelerated by increasing the temperature.

The development inhibitor precursor of this invention is innert with respect to silver halide emulsions and changes very little even under severe preservative condition applied to the photographic materials.

The photosensitive silver halide emulsion used in this invention is a hydrophilic colloidal dispersion of silver chloride, silver bromide, silver chlorobromide, silver iodobromide, silver chloroiodo-bromide or a mixture of them. The halogen composition is selected according to the use and processing condition of the photographic material but the halogen composition as silver bromide, silver iodobromide, or silver chloroiodo-bromide containing less than 10 mol% iodide and less than 30 mol% chloride is particularly preferred.

In this invention, a negative type silver halide emulsion forming surface latent image or a direct reversal silver halide emulsion can be used. As the latter type emulsion, there are an internal latent image-type silver halide emulsion and a pre-fogged direct reversal-type silver halide emulsion.

In this invention internal latent image-type silver halide emulsions are advantageously used, and examples of the emulsions of this type are conversion-type silver halide emulsions, core/shell-type silver halide emulsions, foreign metal-containing silver halide emulsions as disclosed in, for example, U.S. Pat. Nos. 2,592,250, 3,206,313, 3,447,927, 3,761,276 and 3,935,014, etc.

Typical examples of the nucleating agents for the silver halide emulsions of this type are the hydrazines as disclosed in U.S. Pat. Nos. 2,588,982 and 2,563,785; the hydrazines and hydrazones as disclosed in U.S. Pat. No. 3,227,552; the quaternary salt compounds as disclosed in British Pat. No. 1,283,835, Japanese Patent Publication No. 38164/74 and U.S. Pat. Nos. 4,115,122, 3,734,738, 3,719,494 and 3,615,615; the sensitizing dyes having nucleating substituents showing fogging action in the dye molecules as disclosed in U.S. Pat. Nos. 3,718,470; and the thiourea-bound acylhydrazine series compounds as disclosed in U.S. Pat. Nos. 4,030,925, 4,031,127, 4,245,037, 4,255,511, 4,266,013 and 4,276,364, etc.

The silver halide emulsions used in this invention can have enlarged color sensitivity by spectral sensitizing dyes, if desired. Useful spectral sensitizing dyes include cyanine dyes, merocyanine dyes, etc.

The dye image-forming compound used in this invention is of a negative type or a positive type as known in the field of the art; that is, the compound is originally mobile or immobile in the photographic element containing the compound in the case of processing the photographic element with an alkaline processing composition.

Preferred negative-type dye image-forming compounds used in this invention include a coupler capable of releasing or forming a dye upon reaction with an oxidized color developing agent. Specific examples of the coupler are described in U.S. Pat. No. 3,227,550, Canadian Pat. No. 602,607, etc. A preferred negative-type dye image-forming compound used in this invention is a dye-releasing redox compound capable of releasing a dye upon reaction with a developing agent in an oxidized state or with an electron transfer agent. Typical examples of the compound are described in Japanese Patent Publication (Unexamined) Nos. 33826/73, 54021/79, 113624/76 and 71072/82, etc.

As the immobile positive type dye image-forming compound used in this invention, there is a compound releasing a diffusible dye without receiving electrons (i.e., without being reduced) or after receiving at least one electron (i.e., after being reduced) during the photographic processing under an alkaline condition. Typical examples of the compound are described in Japanese Patent Publication (Unexamined) Nos. 111628/74, 63618/76, 4819/77, 69033/78, 110827/78, 110828/78 and 130927/79.

Furthermore, as an effective positive type image-forming compound which is originally mobile under an alkaline photographic processing condition, there are dye developers, and typical examples are described in Japanese Patent Publication Nos. 32130/73 and 22780/80, etc.

The dye formed from the dye image-forming compound used in this invention may be a dye itself or a dye precursor which can be converted into a dye in a photographic processing step or an additional processing step, and further the final image dye may be metallized. As the typical dye structure useful in this invention, there are metallized or non-metallized dyes such as azo dyes, azomethine dyes, anthraquinone dyes, phthalocyanine dyes, etc. Of these dyes, azo series cyan, magenta and yellow dyes are particularly important.

Specific examples of the yellow dye image-forming compound used in this invention are described in Japanese Patent Publication No. 2618/74, U.S. Pat. No. 3,309,199; Japanese Patent Publication No. 12140/82, Japanese Patent Publication (Unexamined) Nos. 114930/76, 111344/79, 16130/81, 71072/81, 79031/79, 64036/78 and 23527/79, U.S. Pat. Nos. 4,148,641 and 4,148,643, and Research Disclosure, 17630 (1978), ibid., 16475 (1977).

Specific examples of the magenta dye image-forming compound are described in U.S. Pat. No. 3,453,107, Japanese Patent Publication No. 43950/71, Japanese Patent Publication (Unexamined) No. 106727/77, U.S. Pat. Nos. 3,932,380, 3,931,144 and 3,932,308, Japanese Patent Publication (Unexamined) Nos. 115528/75, 106727/77, 23628/78, 65034/79, 36804/80, 161332/79, 4028/80, 73057/81, 71060/81, 134/80 and 35533/78, and U.S. Pat. Nos. 4,207,104 and 4,287,292.

Specific examples of the cyan dye image-forming compound are described in Japanese Patent Publication No. 32130/73, Japanese Patent Publication (Unexamined) Nos. 8827/77, 126331/74, 109928/76, 99431/79, 149328/78, 47823/78, 143323/78, 99431/79, 71061/81, 64035/78 and 121125/79, U.S. Pat. Nos. 4,142,891, 4,195,994, 4,147,544 and 4,148,642, European Patents 53,037 and 53,040, and Research Disclosure, 17630 (1978), ibid., 16475 (1975) and ibid., 16475 (1977).

The dye precursor used may be a dye-releasing redox compound having a dye moiety which temporarily shifts the light absorption in a photosensitive element. Specific examples of the redox compound are described in Japanese Patent Publication (Unexamined) Nos. 53330/80 and 53329/80, U.S. Pat. Nos. 3,336,287, 3,579,334 and 3,982,946, and British Pat. No. 1,467,317.

When a dye-releasing redox compound is in processing the photographic elements of this invention, any silver halide developing agents may be used if these developing agents can cross-oxidize the aforesaid redox compound. Such a developing agent may be incorporated in an alkaline processing composition or may be incorporated in a proper layer of the photographic element. Specific examples of the developing agent used in this invention are hydroquinones, aminophenols, phenylenediamines, and pyrazolidinones (e.g., phenidone, 1-phenyl-3-pyrazolidinone, dimezone(1-phenyl-4,4-dimethyl-3-pyrazolidinone), 1-p-tolyl-4-methyl-4-oxymethyl-3-pyrazolidinone, 1-(4'-methoxyphenyl)-4-methyl-oxymethyl-3-pyrazolidinone, 1-phenyl-4-methyl-4-oxymethyl-3-pyrazolidinone, etc.), as disclosed in Japanese Patent Publication (Unexamined) No. 16131/81.

In the foregoing silver halide developing agents, black and white developing agents (in particular, pyrazolidinones) capable of further reducing the formation of stains in an image-receiving layer as compared to a color developing agent such as phenylenediamines are particularly preferred.

When other dye image-forming compounds than the dye-releasing redox compounds are used, an ordinary silver halide developing agent suitable for each dye image-forming compound can be used.

The processing composition used for processing the photographic elements of this invention contains a base such as sodium hydroxide, potassium hydroxide, sodium carbonate, sodium phosphate, etc., and it is proper that the processing composition has a pH of about 9 or higher, preferably 11.5 or higher. The processing composition may further contain an anti-oxidant such as sodium sulfite, an ascorbate, piperidinohexose reductone, etc., or a silver ion concentration controlling agent such as potassium bromide. Moreover, the processing composition may further contain a thickening compound such as hydroxyethyl cellulose, sodium carboxymethyl cellulose, etc.

Still further, the processing composition may contain a compound capable of promoting the development or the diffusion of a dye, such as benzyl alcohol.

For the reproduction of natural color by a substractive color process, a photographic material having at least two combinations of silver halide emulsions each having a selective spectral sensitivity in a certain wavelength region and dye image-forming compounds each having a selective spectral absorption in the same wavelength region.

In particular, a photographic material composed of a combination of a blue-sensitive silver halide emulsion and a yellow dye-releasing redox compound, a combination of a green-sensitive silver halide emulsion and a magenta dye-releasing redox compound, and a combination of a red-sensitive silver halide emulsion and a cyan dye-releasing redox compound is useful. These combination units of the silver halide emulsions and dye-releasing redox compounds may be coated in layers in face-to-face relationship in the photographic material or may be coated in layers as a mixture of particles (a dye-releasing redox compound and a silver halide grain exist in the same particle).

A scavenger for an oxidized developing agent can be used in various interlayers of the photographic elements of this invention. Suitable materials are described in Research Disclosure, Vol. 151, 76–79 (November, 1976).

In this invention, an insulating layer may be formed between the interlayer and the layer containing the dye image-forming compound as disclosed in Japanese Patent Publication (Unexamined) No. 52056/80. Also, a silver halide emulsion may be incorporated in the interlayer or interlayers as disclosed in Japanese Patent Publication (Unexamined) No. 67850/81.

The mordant layers, neutralizing layers, processing compositions, etc., as disclosed in, for example, Japanese Patent Publication (Unexamined) No. 64533/77, can be properly used for the color diffusion transfer photosensitive material of this invention.

The polymer mordant for the image-receiving layer used in this invention is a polymer containing a secondary or tertiary amino group, a polymer having a nitrogen-containing heterocyclic moiety, or a polymer having such a quaternary cation group. The polymer has a molecular weight higher than 5,000, preferably higher than 10,000.

Examples of the mordant used in this invention are vinylpyridine polymers and vinylpyridinium cation polymers as disclosed in U.S. Pat. Nos. 2,548,564, 2,484,430, 3,148,061 and 3,756,814, etc.; vinylimidazolium cation polymers as disclosed in U.S. Pat. No. 4,124,386, etc.; polymer mordants capable of crosslinking with gelatin, etc. as disclosed in U.S. Pat. Nos. 3,625,694, 3,859,096 and 4,128,538, British Pat. No. 1,277,453, etc.; aqueous sol-type mordants as disclosed in U.S. Pat. Nos. 3,958,995, 2,721,852 and 2,798,063, Japanese Patent Publication (Unexamined) Nos. 115228/79, 145529/79, 126027/79, 155835/79 and 17352/81, etc.; water-insoluble mordants as disclosed in U.S. Pat. No. 3,898,088, etc.; reactive mordants capable of making covalent bonding with dyes as disclosed in U.S. Pat. Nos. 4,168,976 and 4,201,840; and mordants as disclosed in U.S. Pat. Nos. 3,709,690, 3,788,855, 3,642,482, 3,488,706, 3,557,066, 3,271,147 and 3,271,148, Japanese Patent Publication (Unexamined) Nos. 30328/78, 155528/77, 125/78, 1024/78 and 107835/78, British Pat. No. 2,064,802, etc.

Further, mordants as disclosed in U.S. Pat. Nos. 2,675,316 and 2,882,156 may be also used in this invention.

As the image-receiving layer for mordanting an azo dye having a chelating group, a layer containing a polymer capable of immobilizing a transition metal ion and a transition metal ion in the mordant layer or a layer adjacent to the mordant layer is preferred. Examples of the polymer capable of immobilizing a transition metal ion are described in Japanese Patent Publication (Unexamined) Nos. 48210/80 and 129346/80, and U.S. Pat. Nos. 4,273,853 and 4,282,305.

The acidic polymers used for the neutralizing layers in this invention are as follows.

A preferred acidic material used as the acidic polymer is a material having an acidic group of less than pKa 9 (or a precursor group capable of providing an acidic group by hydrolysis), and preferred examples thereof are higher fatty acids such as oleinic acid as disclosed in U.S. Pat. No. 2,983,606; polymers of acrylic acid, methacrylic acid or maleic acid or partial esters or acid anhydride thereof as disclosed in U.S. Pat. No. 3,362,819; copolymers of acrylic acid and an acrylic acid ester as disclosed in French Pat. No. 2,290,699; and latex-type acidic polymer as disclosed in U.S. Pat. No. 4,139,383 and Research Disclosure, No. 16102 (1977).

Further, acidic materials as disclosed in U.S. Pat. No. 4,088,493, Japanese Patent Publication (Unexamined) Nos. 153739/77, 1023/78, 4540/78, 4541/78 and 4542/78, etc. may also be used.

Specific examples of the acidic polymer used in this invention are copolymers of ethylene or vinyl monomers such as vinyl acetate, vinyl methyl ether, etc. with maleic anhydride, or n-butyl half esters thereof, a copolymer of butyl acrylate and acrylic acid, cellulose acetate hydrogen phthalate, etc.

The invention will now be further explained practically by the following examples. However, the scope of the invention is not limited to these examples.

EXAMPLE 1

Photographic test of development inhibitor precursor:

A photosensitive material was prepared by coating, in succession, the following layers on a transparent polyethylene terephthalate film support:

(1) A mordant layer containing 3.0 g/m$^2$ of copoly[styrene-N-vinylbenzyl-N,N,N-trihexylammonium chloride] and 3.0 g/m$^2$ of gelatin.

(2) A light-reflecting layer containing 20 g/m$^2$ of titanium dioxide and 2.0 g/m$^2$ of gelatin.

(3) A light-shielding layer containing 3.0 g/m$^2$ of carbon black and 2.0 g/m$^2$ of gelatin.

(4) A layer containing 0.44 g/m$^2$ of a cyan dye-releasing redox compound having the following structure:

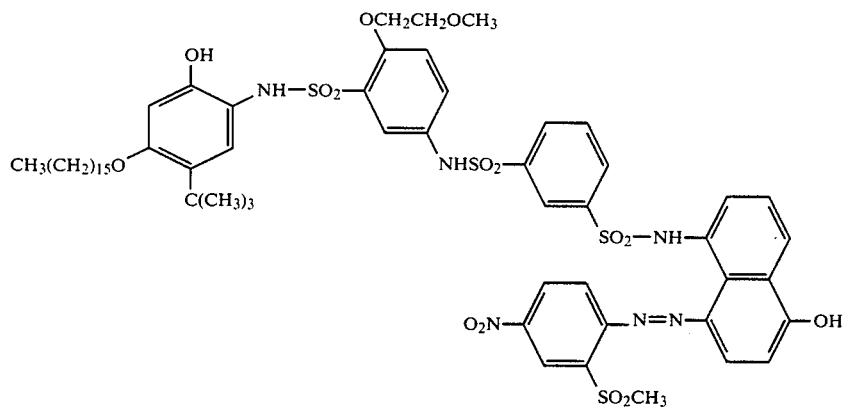

0.09 g/m² of tricyclohexyl phosphate, and 0.8 g/m² of gelatin.

(5) A layer containing 11.5 g/m² (as silver amount) of a red-sensitive internal latent image-type direct reversal silver bromide emulsion, 1.2 g/m² of gelatin, 0.08 g/m² of a nucleating agent having the following structure:

(6) A color mixing preventing agent-containing layer containing 1.0 g/m² of 2,5-di-t-pentadecylhydroquinone and 0.8 g/m² of gelatin.

(7) A layer containing 0.21 g/m² of a magenta dye-releasing redox compound shown by the following structural formula (A), 0.11 g/m² of a magenta dye-releasing redox compound shown by the following structural formula (B), 0.08 g/m² of tricyclohexyl phosphate, and 0.9 g/m² of gelatin.

Structural formula (A):

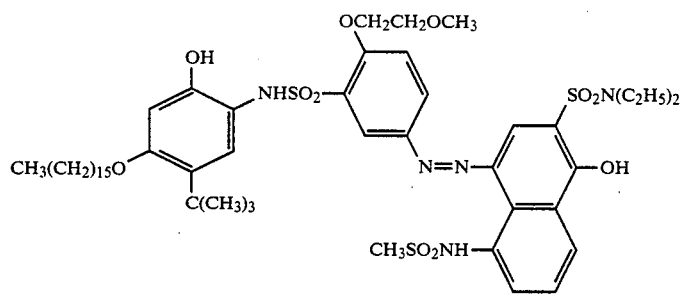

Structural formula (B):

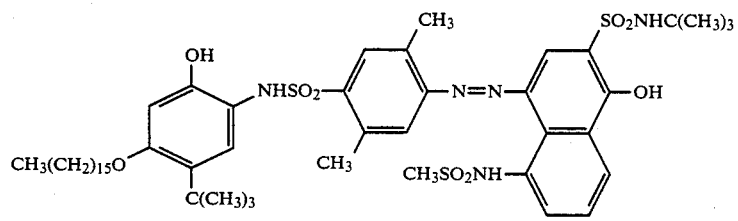

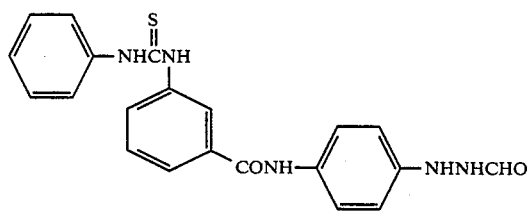

and 0.12 g/m² of 2-sulfo-5-n-pentadecylhydroquinone sodium salt.

(8) A layer containing 0.84 g/m² (as silver amount) of a green-sensitive internal latent image-type direct reversal silver bromide emulsion, 0.9 g/m² of gelatin, 0.04 mg/m² of the same nucleating agent as that in the layer (5), and 0.09 g/m² of 2-sulfo-5-n-pentadecylhydroquinone sodium salt.

(9) A layer same as that of the layer (6).

(10) A layer containing 0.53 g/m² of a yellow dye-releasing redox compound having the following structure:

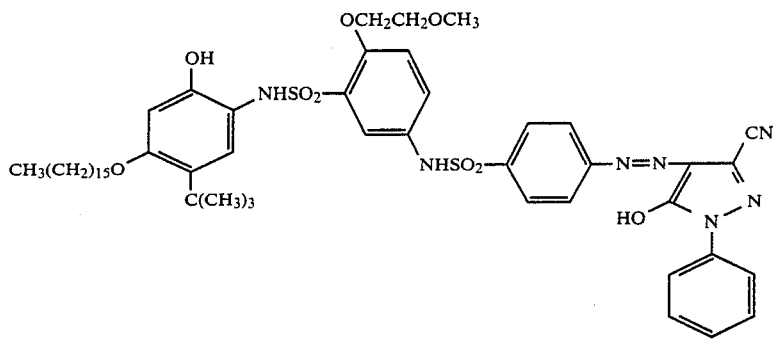

0.13 g/m² of tricyclohexyl phosphate, and 0.7 g/m² of gelatin.

(11) A layer containing 1.12 g/m² (as silver amount) of a blue-sensitive internal latent image-type direct reversal silver bromide emulsion, 1.1 g/m² of gelatin, 0.06 mg/m² of the same nucleating agent as used in the layer (5), and 0.07 g/m² of 2-sulfo-5-n-pentadecylhydroquinone sodium salt.

(12) A layer containing 1.0 g/m² of gelatin.

Now, in the foregoing photosensitive material, each of the development inhibitor precursors of this invention was incorporated in the light-relecting layer (layer (2)) of each photosensitive material in an equivalent amount (0.2 mmols/m²) to provide photosensitive materials of this invention, and these photosensitive materials were compared with the foregoing photosensitive material containing no such precursor and the photosensitive materials each containing following Compound (C) (a compound as disclosed in Japanese Patent Publication (Unexamined) No. 130929/80) and Compound (D) (a compound as disclosed in Japanese Patent Publication (Unexamined) No. 138745/80), respectively.

Compound (C):

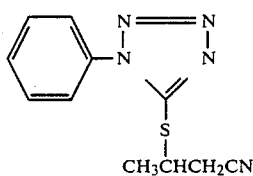

Compound (D):

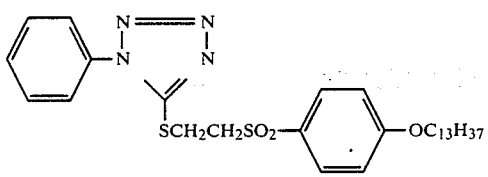

A cover sheet was prepared by coating, in succession, the following layers (1') to (3') on a transparent polyester support.

(1') A layer containing 22 g/m² of a copolymer of acrylic acid and butyl acrylate of 80:20 by weight ratio and 0.44 g/m² of 1,4-bis(2,3-epoxypropoxy)-butane.

(2') A layer containing 3.8 g/m² of acetyl cellulose (forming 39.4 g of acetyl group by hydrolyzing 100 g of acetyl cellulose), 0.2 g/m² of a copolymer (having a molecular weight of about 50,000) of styrene and maleic anhydride of 60:40 by weight ratio, and 0.115 g/m² of 5-(β-cyanoethylthio)-1-phenyltetrazole.

(3') A layer containing 2.5 g/m² of a copolymer latex of vinylidene chloride, methyl acrylate and acrylic acid of 85:12:3 by weight ratio and 0.05 g/m² of a polymethyl methacrylate latex (particle size of 1-3 μm).

Then, a processing composition having the following formulation was prepared.

| | |
|---|---|
| 1-p-Tolyl-4-hydroxymethyl-4-methyl-3-pyrazolidone | 12.0 g |
| Methylhydroquinone | 0.3 g |
| 5-Methylbenzotriazole | 3.5 g |
| Sodium sulfite (anhydrous) | 0.2 g |
| Na salt of carboxymethyl cellulose | 58 g |
| Potassium hydroxide (28% aq. soln.) | 200 ml |
| Benzyl alcohol | 1.5 ml |
| Carbon black | 150 g |
| Water | 685 ml |

After exposing each of the photosensitive materials thus prepared through a multicolor wedge, the photosensitive material was united with a container containing the aforesaid processing composition and the cover sheet, and then the processing composition was spread between the photosensitive material and the cover sheet by means of a pressure-applying member in a thickness of 80 μm.

(a) Effect of processing temperature to Dmin:

The foregoing processing was performed at 10° C. or 35° C., the density of each transferred image after one day was measured by means of a color densitometer. The values of the Dmin in the processings at 10° C. and 35° C., and the difference ΔDmin between Dmin (35° C.) and Dmin (10° C.) are shown in Table 1.

As the ΔDmin decreases, the change of the color image by the processing temperature decreases, that is, the allowable range of the processing temperature is wider.

TABLE 1

| Sample No. | Compound No. | 10° C. Dmin | | | 35° C. Dmin | | | Δ Dmin | | |
|---|---|---|---|---|---|---|---|---|---|---|
| | | Yellow | Magenta | Cyan | Yellow | Magenta | Cyan | Yellow | Magenta | Cyan |
| 1 | — | 0.24 | 0.25 | 0.36 | 0.29 | 0.29 | 0.48 | +0.05 | +0.04 | +0.12 |
| 2 | C | 0.21 | 0.22 | 0.32 | 0.24 | 0.25 | 0.37 | +0.03 | +0.03 | +0.05 |

TABLE 1-continued

| Sample No. | Compound No. | 10° C. Dmin | | | 35° C. Dmin | | | Δ Dmin | | |
|---|---|---|---|---|---|---|---|---|---|---|
| | | Yellow | Magenta | Cyan | Yellow | Magenta | Cyan | Yellow | Magenta | Cyan |
| 3 | D | 0.22 | 0.23 | 0.32 | 0.24 | 0.25 | 0.37 | +0.02 | +0.02 | +0.05 |
| 4 | 1 | 0.23 | 0.24 | 0.33 | 0.24 | 0.26 | 0.38 | +0.01 | +0.02 | +0.05 |
| 5 | 2 | 0.22 | 0.25 | 0.32 | 0.24 | 0.27 | 0.38 | +0.02 | +0.02 | +0.06 |
| 6 | 4 | 0.22 | 0.24 | 0.34 | 0.25 | 0.26 | 0.38 | +0.03 | +0.02 | +0.04 |
| 7 | 5 | 0.21 | 0.23 | 0.33 | 0.24 | 0.27 | 0.37 | +0.03 | +0.04 | +0.04 |

From the results of Table 1, it has been confirmed that any of the compounds used in the test have an effect of reducing the Dmin and also show low Dmin values as compared to the case of not adding such a compound.

(b) Shelf life of photosensitive material:

On each of the photosensitive materials preserved for 3 days in a room (25° C., 60% RH) or for 3 days at 60° C., 70% RH, the processing composition was spread at 25° C., and after one day, the transferred image was measured by means of a color densitometer. Then, the Dmax value in each case and the difference ΔDmax between the Dmax (preserved in the room) and the Dmax (preserved at 60° C., 70% RH) are shown in Table 2.

TABLE 2

| Sample No. | Compound No. | Room (25° C., 60% RH), 3 Days Dmax | | | 50° C., 70% RH 3 Days Dmax | | | Δ Dmax | | |
|---|---|---|---|---|---|---|---|---|---|---|
| | | Yellow | Magenta | Cyan | Yellow | Magenta | Cyan | Yellow | Magenta | Cyan |
| 1 | — | 1.80 | 2.10 | 2.22 | 1.75 | 1.82 | 1.95 | +0.05 | +0.28 | +0.27 |
| 2 | C | 1.82 | 2.12 | 2.21 | 1.51 | 1.24 | 1.36 | +0.31 | +0.88 | +0.85 |
| 3 | D | 1.81 | 2.11 | 2.20 | 1.64 | 1.31 | 1.38 | +0.17 | +0.80 | +0.82 |
| 4 | 1 | 1.82 | 2.14 | 2.19 | 1.72 | 1.81 | 1.92 | +0.10 | +0.33 | +0.29 |
| 5 | 2 | 1.81 | 2.13 | 2.18 | 1.73 | 1.83 | 1.93 | +0.08 | +0.30 | +0.25 |
| 6 | 4 | 1.83 | 2.12 | 2.19 | 1.72 | 1.82 | 1.90 | +0.11 | +0.30 | +0.29 |
| 7 | 5 | 1.82 | 2.11 | 2.22 | 1.75 | 1.80 | 1.93 | +0.07 | +0.31 | +0.29 |

As is clear from the results shown in Table 2, the compounds of this invention show less reduction in Dmax as compared to the comparison compounds.

From the results of the foregoing tests (a) and (b), it has been confirmed that the compounds of this invention are effective for the reduction in Dmin, and further that the photosensitive materials containing the compounds of this invention are excellent in shelf life as compared to photosensitive materials containing conventional compounds.

While the invention has been described in detail and with reference to specific embodiments thereof, it will be apparent to one skilled in the art that various changes and modifications can be made therein without departing from the spirit and scope thereof.

What is claimed is:

1. A photographic element comprising a support having provided thereon at least one photosensitive silver halide emulsion layer, said photographic element containing a development inhibitor precursor represented by following general formula (I):

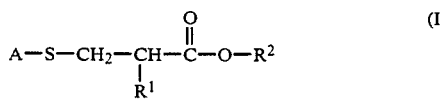

wherein A represents an unsubstituted or substituted phenyl group or a 5-membered or 6-membered nitrogen-containing heterocyclic ring; $R^1$ represents a hydrogen atom or a monovalent substituent; and $R^2$ represents an organic ballasting group.

2. A photographic element as claimed in claim 1, wherein the element is a color diffusion transfer photographic element.

3. A photographic element as claimed in claim 2, further comprising:
a dye image-forming compound associated with the emulsion layer;
an image-receiving element for fixing a diffusible dye formed from the dye image-forming compound to form an image;
an alkaline processing composition capable of developing the exposed photosensitive element; and
a neutralizing means for neutralizing the alkaline processing composition.

4. A photosensitive element as claimed in claim 1, wherein A is a tetrazole ring.

5. A photographic element as claimed in claim 4, wherein A is a phenyltetrazole ring.

6. A photographic element as claimed in claim 2, wherein the color diffusion transfer photographic element comprises:
a photosensitive sheet comprising a transparent support having provided thereon an image-receiving element for fixing a diffusible dye to form an image, a white reflecting layer, a light-shielding layer, and a photosensitive element including at least one silver halide emulsion layer and a dye image-forming compound associated therewith;
an alkaline processing composition capable of developing the exposed photosensitive element; and
a cover sheet comprising another support having provided thereon a neutralizing means for neutralizing the alkaline processing composition.

7. A photographic element as claimed in claim 1, wherein A is a substituted tetrazole ring.

8. A photographic element as claimed in claim 1, wherein the silver halide emulsion layer is in internal latent image-type direct positive silver halide emulsion layer.

9. A photographic element as claimed in claim 8, wherein the dye image-forming compound associated with the internal latent image-type direct positive silver halide emulsion layer is dye-releasing redox compound.

10. A photographic element as claimed in claim 1, wherein the development inhibitor precursor is a compound represented by following general formula (II):

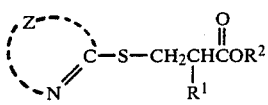 (II)

wherein Z represents a non-metallic atomic group necessary for completing a 5-membered or 6-membered heterocyclic ring, and $R^1$ and $R^2$ are the same as defined in claim 1.

11. A photographic element as claimed in claim 1, wherein the development inhibitor precursor is present in an amount of at least $10^{-5}$ mol per mol of silver.

12. A photographic element as claimed in claim 11, wherein the development inhibitor precursor is present in an amount in the range of $10^{-4}$ to $10^{-1}$ mol per mol of silver.

13. A photographic element as claimed in claim 1, wherein A includes the moiety:

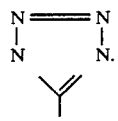

14. A photographic element as claimed in claim 13, wherein said moiety is substituted with a phenyl group, which phenyl group may also be substituted.

15. A photographic element as claimed in claim 14 wherein the organic ballasting group is a substituted or unsubstituted alkyl group having 8 to 32 carbon atoms.

* * * * *